(12) United States Patent
Roberts

(10) Patent No.: US 10,016,337 B2
(45) Date of Patent: Jul. 10, 2018

(54) DEVICE AND METHOD FOR TRIGGER POINT MASSAGE THERAPY

(71) Applicant: PSOAS Massage Therapy Offices, P. C., New York, NY (US)

(72) Inventor: Michelle G. Roberts, New York, NY (US)

(73) Assignee: PSOAS MASSAGE THERAPY OFFICES, P.C., New York, NY (US)

( * ) Notice: Subject to any disclaimer, the term of this patent is extended or adjusted under 35 U.S.C. 154(b) by 742 days.

(21) Appl. No.: 14/525,164

(22) Filed: Oct. 27, 2014

(65) Prior Publication Data

US 2015/0119771 A1   Apr. 30, 2015

Related U.S. Application Data

(60) Provisional application No. 61/907,342, filed on Nov. 21, 2013, provisional application No. 61/896,610, filed on Oct. 28, 2013.

(51) Int. Cl.
*A61H 39/00* (2006.01)
*A61H 39/04* (2006.01)
(Continued)

(52) U.S. Cl.
CPC ......... *A61H 39/04* (2013.01); *A61H 23/0218* (2013.01); *A61N 1/26* (2013.01); *A61N 5/0619* (2013.01); *A61H 23/0245* (2013.01); *A61H 2201/0153* (2013.01); *A61H 2201/02* (2013.01); *A61H 2201/10* (2013.01);
(Continued)

(58) Field of Classification Search
CPC ................ A61H 39/04; A61H 23/0218; A61H 2201/5071; A61H 2201/501; A61H 2201/5007; A61H 2201/50; A61H 2201/1685; A61H 2201/168; A61H 2201/1671; A61H 2201/10; A61H 23/0245; A61H 2201/0153; A61H 2201/02; A61N 1/26; A61N 5/0619; A61N 2005/067; A61N 2005/0659; A61N 2005/0644
See application file for complete search history.

(56) References Cited

U.S. PATENT DOCUMENTS

| 854,983 A | 5/1907 | Clark |
| 3,710,785 A | 1/1973 | Hilger |
| (Continued) | | |

*Primary Examiner* — Quang D Thanh
(74) *Attorney, Agent, or Firm* — Olav M. Underdal; IDP Patent Services

(57) ABSTRACT

A trigger point massage therapy device for well-controlled trigger point therapy, suitable for long-term use by a health practitioner with minimal risk of pain or injury, can include a main body with a handle, rubberized grips, a connection pin, that can connect to a pressure point base with a pressure point tip, whereon can further be installed additional pressure point tips in different sizes; a pressure sensor, a step-vibration component, an electro-motor; and additionally heating, ultra sound, electrical stimulation, infrared, and cold laser light components. The device can further include a control unit, which can be used for programming and controlling the functions of the device. Also described is a method for trigger point massage therapy, including measuring a pressure, adjusting the pressure, holding the pressure, rotating/unwinding, vibrating, and increasing the pressure.

22 Claims, 9 Drawing Sheets

(51) Int. Cl.
  *A61H 23/02* (2006.01)
  *A61N 5/06* (2006.01)
  *A61N 1/26* (2006.01)
  *A61N 5/067* (2006.01)

(52) U.S. Cl.
  CPC .................. *A61H 2201/168* (2013.01); *A61H 2201/1671* (2013.01); *A61H 2201/1685* (2013.01); *A61H 2201/50* (2013.01); *A61H 2201/501* (2013.01); *A61H 2201/5007* (2013.01); *A61H 2201/5071* (2013.01); *A61N 2005/067* (2013.01); *A61N 2005/0644* (2013.01); *A61N 2005/0659* (2013.01)

(56) References Cited

U.S. PATENT DOCUMENTS

| | | |
|---|---|---|
| 4,669,452 A | 6/1987 | Osawa |
| 5,063,911 A | 11/1991 | Teranishi |
| 5,065,743 A | 11/1991 | Sutherland |
| 5,103,809 A | 4/1992 | Deluca |
| 5,183,034 A | 2/1993 | Yamasaki |
| 5,352,188 A | 10/1994 | Vitko |
| 5,356,369 A | 10/1994 | Yamasaki |
| 5,899,868 A | 5/1999 | Vandeberg |
| 6,010,467 A | 1/2000 | Smith |
| 6,267,738 B1 | 7/2001 | Louis |
| 7,153,282 B1 | 12/2006 | Dudley |
| 2003/0009116 A1* | 1/2003 | Luettgen ............... A61H 19/34 601/46 |
| 2007/0270727 A1* | 11/2007 | Khorassani Zadeh . A61H 1/008 601/120 |
| 2008/0139981 A1 | 6/2008 | Walquist |
| 2009/0210027 A1* | 8/2009 | Wise ...................... A61H 21/00 607/46 |
| 2009/0240176 A1* | 9/2009 | Clementes ............. A61H 7/003 601/135 |
| 2014/0163437 A1* | 6/2014 | Mack ..................... A61H 19/30 601/46 |
| 2014/0309565 A1* | 10/2014 | Allen ..................... A61H 19/44 601/46 |

* cited by examiner

Massage Therapy Trigger Point Device

722

722

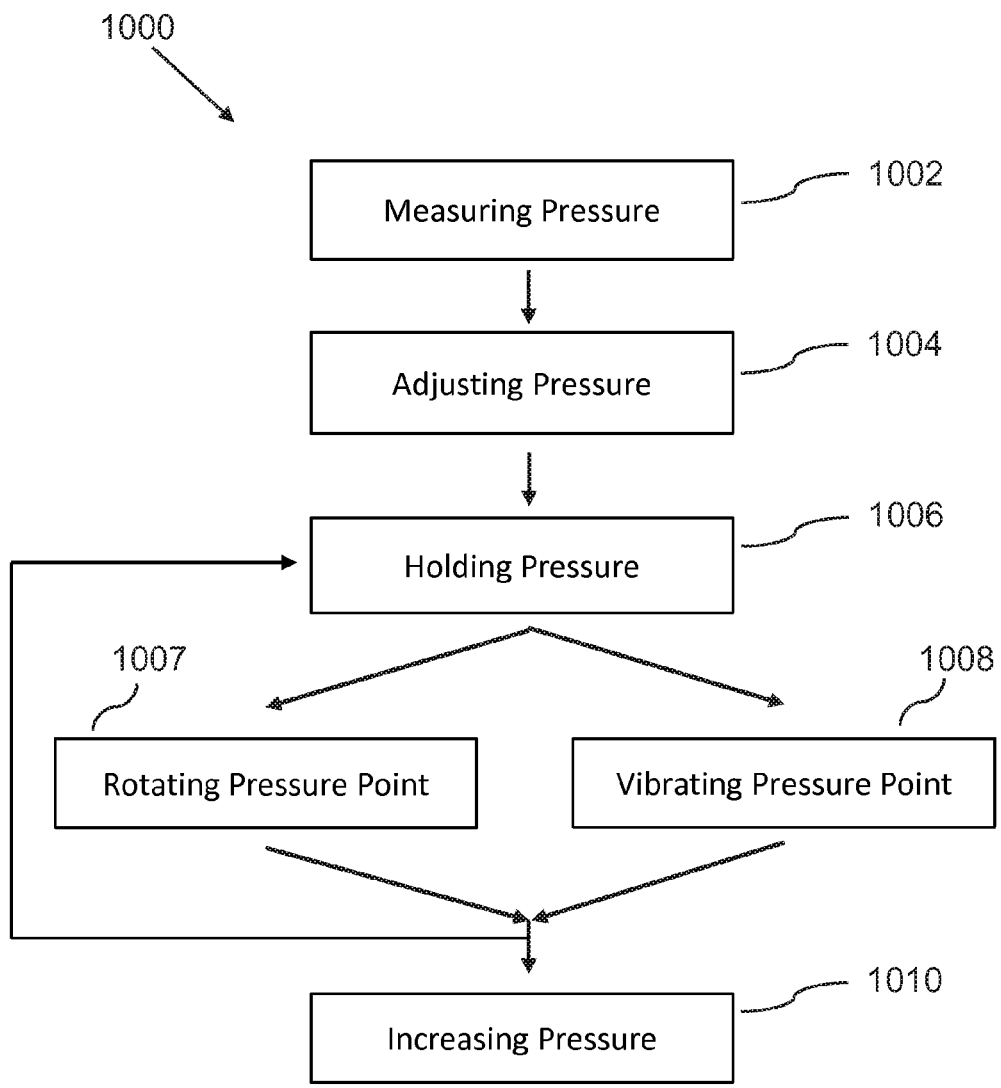

DEVICE AND METHOD FOR TRIGGER POINT MASSAGE THERAPY

CROSS-REFERENCE TO RELATED APPLICATIONS

This application claims the benefit of U.S. Provisional Application No. 61/907,342, filed Nov. 21, 2013, and U.S. Provisional Application No. 61/896,610, filed Oct. 28, 2013.

FIELD OF THE INVENTION

The present invention relates generally to the field of devices and methods for massage therapy, and herein particularly trigger point and neuromuscular therapy.

BACKGROUND OF THE INVENTION

Trigger points, also known as trigger sites or muscle knots, are hyperirritable spots in skeletal muscle that are associated with palpable nodules in taut bands of muscle fibers.

Trigger points will often cause otherwise unexplained pain that radiates from such points of local tenderness to related areas, sometimes not immediately adjacent to the trigger point itself.

Trigger points are caused by muscle exertion, overuse, repetitive stress, bio-mechanical and postural overload. Overload is when a muscle is placed in an over shortened or overstretched state for a prolonged period of time. Deep thumb or elbow pressure is applied to relief muscular pain and dysfunction causing the trigger points to deactivate.

A trigger point is described as a clinical finding with the following symptoms:
 a. Pain related to a discrete, irritable point in skeletal muscle or fascia, not caused by acute local trauma, inflammation, degeneration, neoplasm or infection.
 b. The painful point can be felt as a nodule or band in the muscle, and a twitch response can be elicited on stimulation of the trigger point.
 c. Palpation of the trigger point reproduces the patient's complaint of pain, and the pain radiates in a distribution typical of the specific muscle harboring the trigger point.
 d. The pain cannot be explained by findings on neurological examination.

Health professionals, such as neurologist, osteopaths, orthopedic doctors, chiropractors, occupational therapists, physical therapists, acupuncturists, and massage therapists can identify trigger points as the cause of radiating or localized pain, and initiate various related treatment regimes.

The most common treatment approach is controlled application of pressure ischemic compression. Therapists will often use thumb, elbows, or simple mechanical tools to apply pressure directly upon the trigger point, in order to reduce strain on their hands. Therapists will often develop joint tenderness and injuries to hands and fingers as a consequence of long-term treatment of patients, due to the reactive forces and pressure manifesting in the arms, elbows, hands and fingers of the practitioner during trigger point treatment sessions.

The benefits of trigger point therapy include:
 a. Aids in deactivating trigger points;
 b. Reduces muscle contraction and muscle spasm;
 c. Reduces muscle overload and pain patterns
 d. Reduces adhesion and nodules;
 e. Restores muscle function and regeneration;
 f. Increases muscle length, flexibility and elasticity
 g. Increases motor function and range of motion;
 h. Increases blood flow, muscle relaxation and nutrients to localize areas The results of manual therapy are related to the skill level of the therapist. If trigger points are pressed for too short a time, they may activate or remain active; if pressed too long or hard, they may be irritated or the muscle may be bruised, resulting in pain in the area treated.

As such, considering the foregoing, it may be appreciated that there continues to be a need for novel and improved physiotherapeutic devices and methods for treatment of trigger points.

SUMMARY OF THE INVENTION

The foregoing needs are met, to a great extent, by the present invention, wherein in aspects of this invention, enhancements are provided to the existing model of trigger point therapy In an aspect, a trigger point massage therapy device can include a main body with a soft palm pressure pad, a pressure point tip for application of pressure to a patient, and a handle with rubberized grip points, whereby a therapist can apply well-controlled pressure with one or two-handed operation.

In a related aspect, the therapist can employ functions to monitor the applied pressure and compare that to a target pressure level.

In a related aspect, the device can apply rotation, vibration and forward/backward tip movement, which can increase or decrease applied pressure in increments of a predetermined duration, specified in milliseconds In further related aspects, the device can also provide heating, cold laser light, infrared, ultrasound, electrical stimulation, and other common therapeutic methods and functions.

In a related aspect, a method for trigger point massage therapy can include measuring a pressure, adjusting the pressure, holding the pressure, rotating/unwinding and/or vibrating, and increasing the pressure.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. In addition, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the

BRIEF DESCRIPTION OF THE DRAWINGS

FIG. 10 is a schematic diagram of a method or process for trigger point massage therapy, according to an embodiment of the invention.

DETAILED DESCRIPTION

Before describing the invention in detail, it should be observed that the present invention resides primarily in a novel and non-obvious combination of elements and process steps. So as not to obscure the disclosure with details that will readily be apparent to those skilled in the art, certain conventional elements and steps have been presented with lesser detail, while the drawings and specification describe in greater detail other elements and steps pertinent to understanding the invention.

The following embodiments are not intended to define limits as to the structure or method of the invention, but only to provide exemplary constructions. The embodiments are permissive rather than mandatory and illustrative rather than exhaustive.

An embodiment of a trigger point massage therapy device describes a handheld device for single hand or dual hand operation that can facilitate well-controlled ischemic compression/trigger point therapy, and is suitable for long-term use by massage therapists and other health practitioners, with minimal risk of pain or injury.

In a related embodiment, a health practitioner can apply pressure via one or two-handed operation, and can monitor that actual pressure applied is approximately equal to a displayed target pressure.

In a related embodiment, various programs and controls can be selected via an attached control unit.

Figure 1:
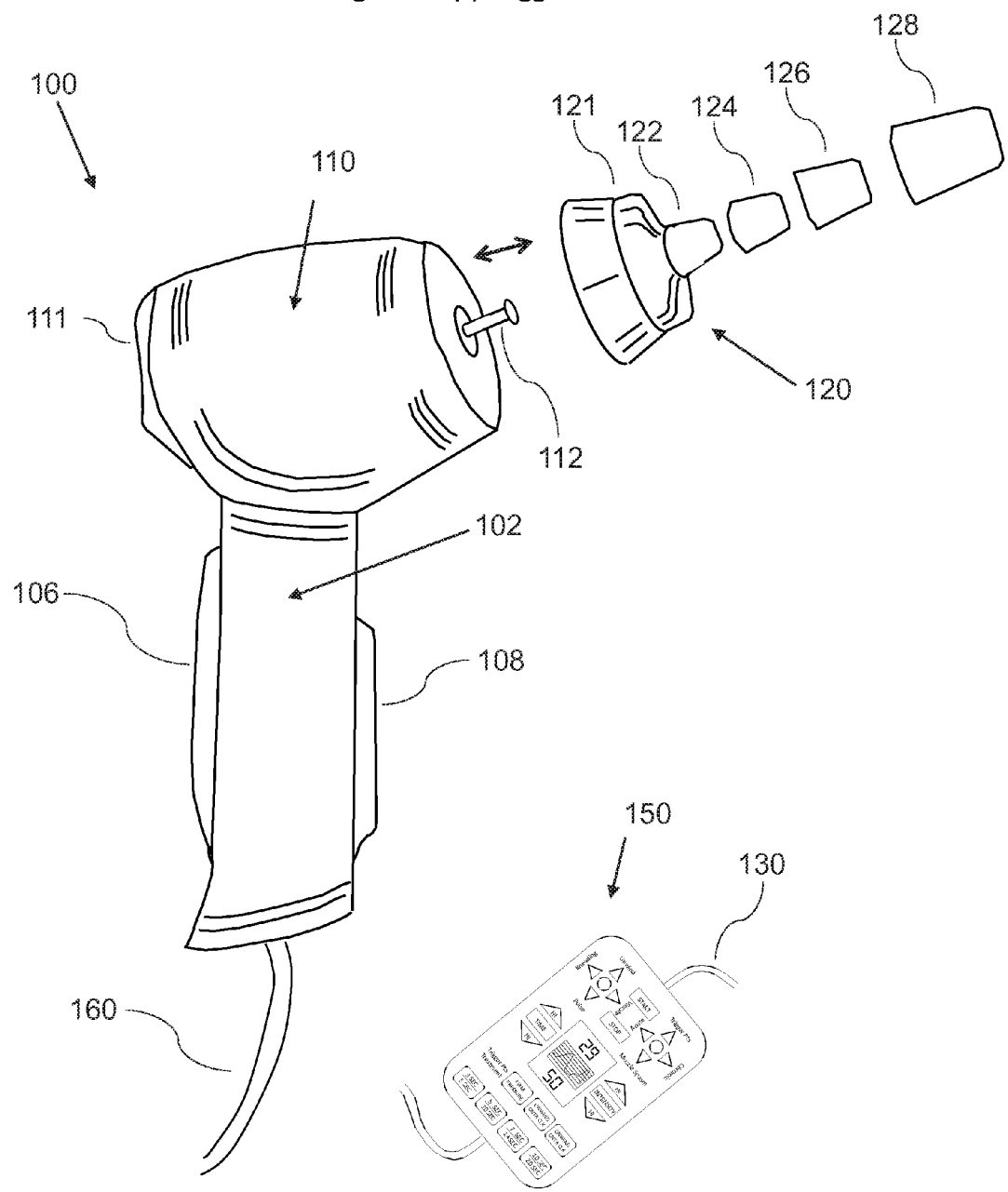
FIG. 1 is a perspective view of a trigger point massage therapy device, according to an embodiment of the invention.

In the following we describe the structure of such an embodiment in the form of trigger point massage therapy device with reference to FIG. 1, in such manner that like reference numerals refer to like components throughout; a convention that we shall employ for the remainder of this specification.

A trigger point massage therapy device 100 can include
a. A main body 110, which can further include
  i. A soft palm pressure pad 111, which for example can be an overmolded rubber component, to allow a therapist to apply additional pressure with the palm of a second hand.
  ii. A connection pin 112, for example manufactured in metal or other suitable material; and
  iii. A pressure point tip 122, which is connected to the connection pin, for example via snap-lock, screw, or other fastening mechanism, and can be manufactured in a rubber or silicone material;
b. A handle 102, wherein the handle can be a pistol-type grip or some other ergonomic handle configuration, which can be manufactured in plastic or other suitable material, and can further comprise
  i. A soft rear hand grip 106;
  ii. A soft front hand grip 108;
  Wherein both the soft rear hand grip 106 and the soft front hand grip 108 for example can be over molded rubber components, which in conjunction enable improved comfort and hold, when gripped by a first hand of the practitioner;
c. A power and control cable 160;
d. A control unit 150, which can be configured to program and control the functions of the trigger point massage therapy device 100, via the control cable 160;
e. A power cable 130.

In a related embodiment, a pressure point tip can further include a pressure point base 121, which has a main pressure point tip 122, where-on can further be installed, additional pressure point tips 124, 126, 128, of different sizes, which can be manufactured in a rubber material;

In related embodiments, the pressure point tips 122 124 126 128 can be made of materials of different hardness and friction. In some embodiments the pressure point tips 122 124 126 128 can be a soft, medium or hard rubber material.

In alternative embodiments, the pressure point tips 122 124 126 128 can be made of a soft, medium or hard silicone material.

In yet other alternative embodiments, the pressure point tips 122 124 126 128 can be a made from plastic materials, which can be suitable for application where a harder pressure point tip is needed.

Figure 2:
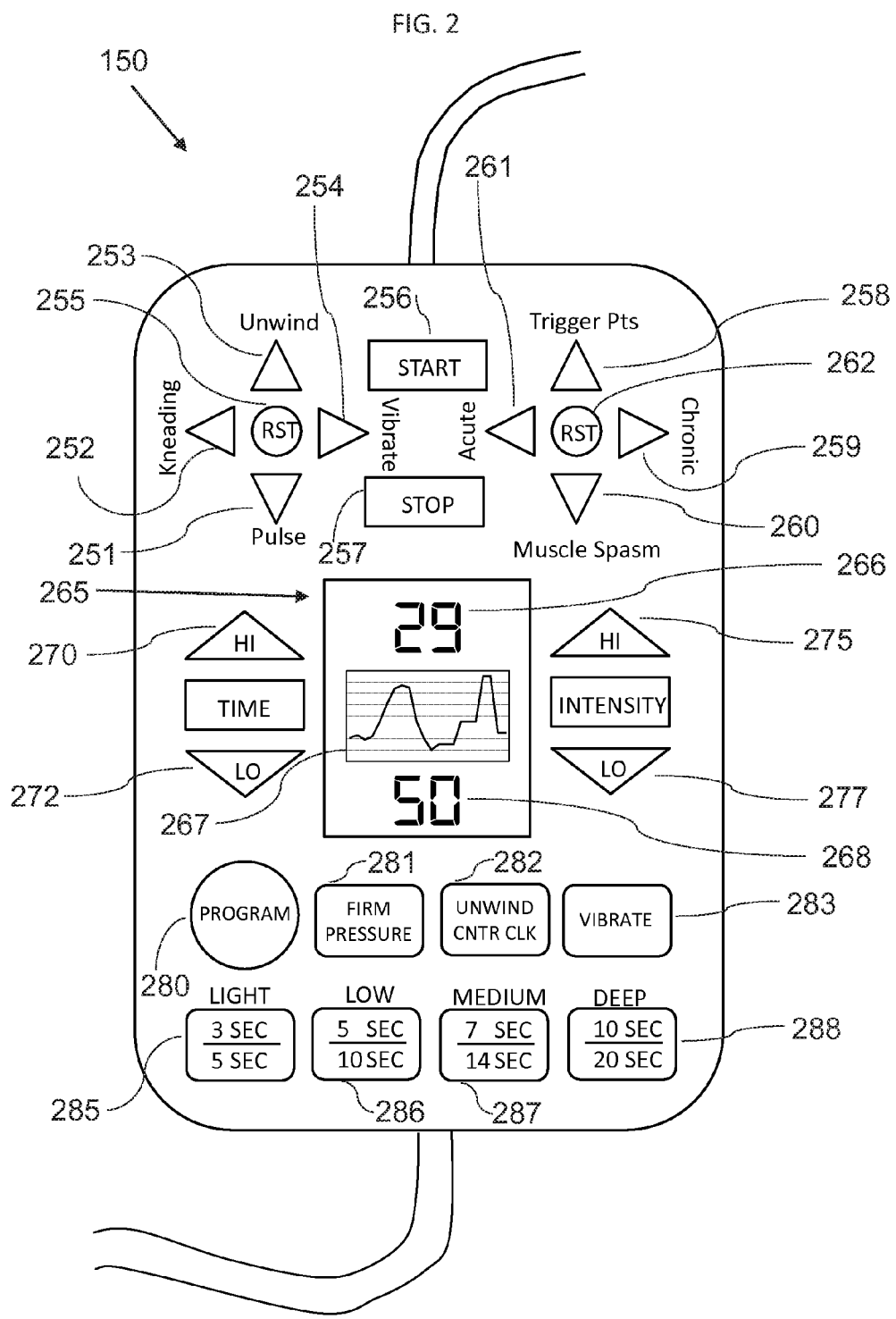
FIG. 2 is a front view of a control unit of a trigger point massage therapy device, according to an embodiment of the invention.
Figure 3:
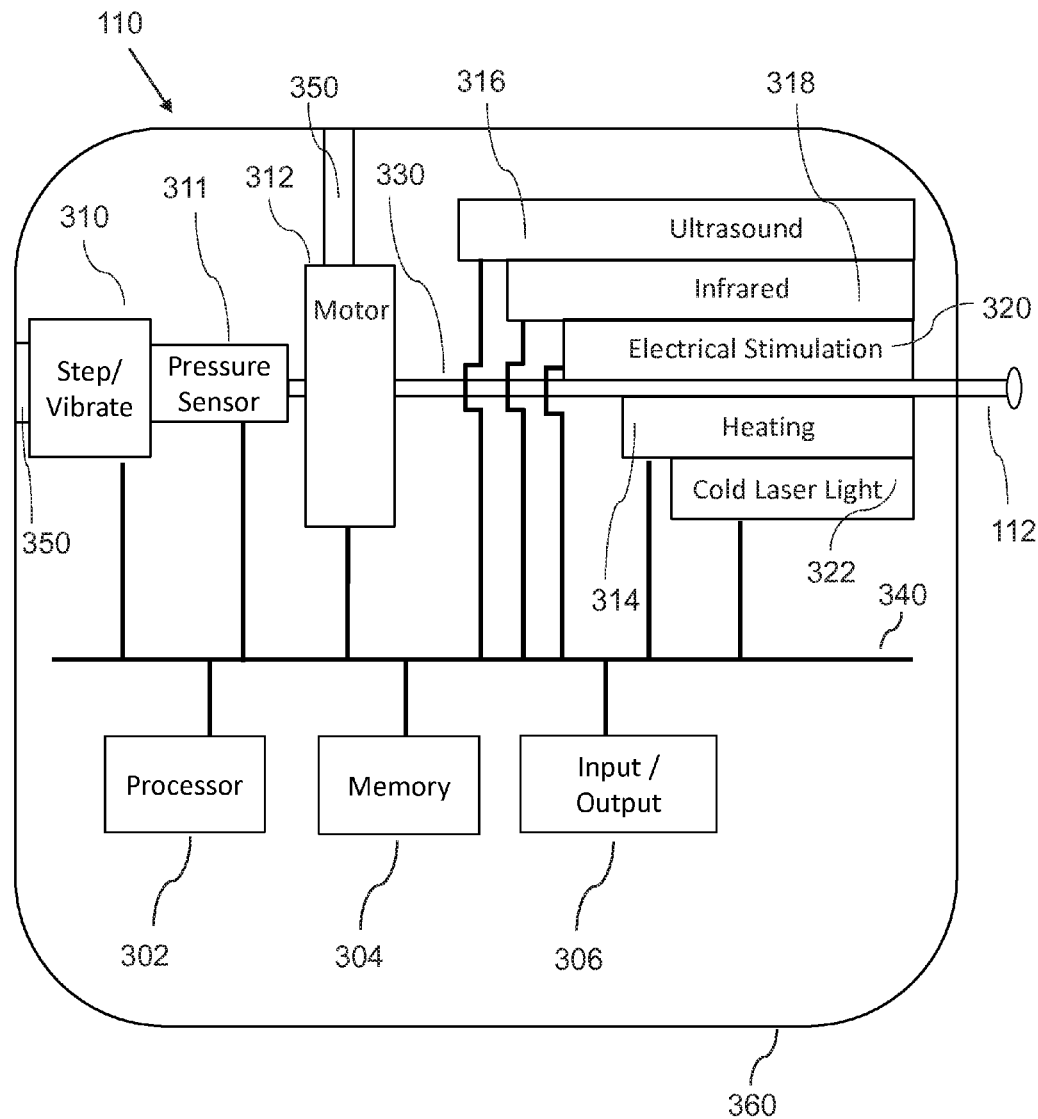
FIG. 3 is a schematic diagram of a trigger point massage therapy device, according to an embodiment of the invention.

In an embodiment, illustrated in FIG. 2, the control unit 150 can include:
a. A start button 256, for starting a therapy session;
b. A stop button 257, for ending a therapy session;
c. A pulse button 251, for switching to the pulse function, which starts a pulsating pattern emitted via the connection pin 112 and transferred to the main pressure point tip 122.
d. A kneading button 252, for switching to the kneading function, which starts a kneading pattern emitted via the connection pin 112 and transferred to the main pressure point tip 122.
e. An unwind button 253, for switching to the unwind function, which starts an unwind pattern, in the form of a counter-clock rotation, emitted via the connection pin 112 and transferred to the main pressure point tip 122.

f. A vibrate button 254, for switching to the vibrate function, which starts a vibration pattern emitted via the connection pin 112 and transferred to the main pressure point tip 122.

g. A function reset button 255, for resetting the selected function to neutral;

h. A trigger point button 258, for switching to the trigger point mode, which selects a trigger point mode adjustment of the selected function pattern 251 252 253 254.

i. A chronic pain button 259, for switching to the chronic pain mode, which selects a chronic pain mode adjustment of the selected function pattern 251 252 253 254.

j. A muscle spasm button 260, for switching to the muscle spasm mode, which selects a muscle spasm mode adjustment of the selected function pattern 251 252 253 254.

k. An acute pain button 261, for switching to the acute pain mode, which selects an acute pain mode adjustment of the selected function pattern 251 252 253 254.

l. A mode reset button 262, for resetting the selected mode to neutral;

m. A pressure indicator 265, further including
  i. An actual pressure indicator 266, which displays the current actual pressure, for example on a relative scale from 0 to 100, as applied by a therapy practitioner.
  ii. A pressure status graph indicator 267, which displays a historical graph of the pressure applied in the last X seconds, and a planned graph of the pressure targeted or planned by the selected settings to be applied in the next X seconds. X is a predetermined value, which for example can be 60 seconds.
  iii. A target pressure indicator 268, which displays the pressure currently targeted or planned, in accordance with selected settings.

n. A time increase button 270, for lengthening the treatment time;

o. A time decrease button 272, for shortening the treatment time;

p. An intensity increase button 275, for increasing the treatment intensity;

q. An intensity lowering button 277, for decreasing the treatment intensity;

r. A program select button 280, for cycling through a plurality of pre-determined programs;

s. A firm pressure button 281, for selecting the firm pressure function, which can increase the pressure in time-intervals of a predetermined number of milliseconds, via outward movement of the connection pin 112;

t. An unwind button 282, for selecting the unwind function, which initiates a counter clock-wise unwind rotation to relax the trigger point muscles;

u. A vibrate button 283, for selecting the vibrate function;

v. A light program adjustment button 285, for selecting a light intensity program, wherein the targeted pressure, as indicated on the pressure status graph indicator 267 and the target pressure indicator 268, is gradually increased from zero for 3 seconds, and then maintained for 5 seconds;

w. A low program adjustment button 286, for selecting a low intensity program, wherein the targeted pressure, as indicated on the pressure status graph indicator 267 and the target pressure indicator 268, is gradually increased from zero for 5 seconds, and then maintained for 10 seconds;

x. A medium program adjustment button 287, for selecting a medium intensity program, wherein the targeted pressure, as indicated on the pressure status graph indicator 267 and the target pressure indicator 268, is gradually increased from zero for 7 seconds, and then maintained for 14 seconds;

y. A deep program adjustment button 288, for selecting a deep intensity program, wherein the targeted pressure, as indicated on the pressure status graph indicator 267 and the target pressure indicator 268, is gradually increased from zero for 10 seconds, and then maintained for 20 seconds;

In an embodiment, illustrated in FIG. 3, the main body 110 can include the following internal components:

a. A processor 302;

b. A memory 304;

c. An input/output component 306;

d. An axle 330, which is connected to the connection pin 112;

e. A step-vibration component 310, which can be configured to produce a vibration and longitudinal movement of the axle 330, wherein an outward movement can momentarily increase the pressure, such that a sequence of outward movement steps, in increments of a predetermined duration, specified in milliseconds, can increase the pressure in increments, and a sequence of inward movements can similarly decrease the pressure;

f. A pressure sensor component 311, which is connected to the axle 330, such that the pressure sensor component 311 can measure a pressure applied to the pressure point tip, which is transmitted via the connection pin 112 and the axle 330, so that the axle 330 applies the transmitted pressure to the pressure sensor component 311;

g. An electro-motor 312, which can be configured to rotate the axle 330, both clockwise and counter-clockwise, under control by the processor 302;

h. A heating component 314, which can heat the connection pin 112, whereby attached tips can be heated;

i. A ultrasound component 316, which can target the treatment area with ultrasound applied close to the treatment tip connected to the connection pin 112, and radiated either via an ultrasound aperture in the surface of the main body 110, or via the axle 330 and the connection pin 112;

j. An infrared component 318, which can radiate the treatment area with infrared radiation targeting the area close to the treatment tip connected to the connection pin 112, and radiated via an infrared aperture in the surface of the main body 110;

k. An electrical stimulation component 320, which can stimulate the treatment area with electrical stimulation targeting the area close to the treatment tip connected to the connection pin 112, and transmitted via the axle 330 and the connection pin 112; and l. A cold laser light component 322, which can radiate the treatment area with cold laser light targeting the area close to the treatment tip connected to the connection pin 112, and radiated via a cold laser light aperture in the surface of the main body 110; wherein all components are connected via m. A data bus 340.

In various embodiments, the trigger point massage therapy device 100 can be manufactured in consumer, prosumer/semi-professional, and professional variants for use in both home and clinical environments.

In a related embodiment, the step-vibration component 310 can be connected to a frame 360 of the main body 110, via a frame connection 350, in order to transmit pressure/force applied by a user of the trigger point massage therapy device 100.

In a related embodiment, the pressure sensor 311 can be connected to a frame 360 of the main body 110, via a frame connection 350, in order to transmit pressure/force applied by a user of the trigger point massage therapy device 100.

In FIG. 3, the pressure sensor 311 is shown connected indirectly to the frame 360, via the step-vibration component 310. In alternative embodiments, the step-vibration component 310 can be connected indirectly to the frame 360, via the pressure sensor 311, or both the step-vibration component 310 and the pressure sensor 311 can be connected directly to the frame 360.

In a related embodiment, the electro-motor 312 can be connected to a frame 360 of the main body 110, via a frame connection 350, in order to rotate the axle 330 relative to the frame 360 of the main body 110.

In a related embodiment, the handle 102 can be connected to the frame 360 of the main body 110.

In a related embodiment, an outward step of the step-vibration component 310 can cause an outward movement of the axle in a range of 0.5 mm to 5 mm. Similarly, an inward step of the step-vibration component 310 can cause an inward movement of the axle in a range of 0.5 mm to 5 mm. Depending on the application, these ranges can be larger or smaller.

In a related embodiment, the step-vibration component 310 can be a linear actuator, for example based on a piezoelectric or electro-mechanical design, such that the step-vibration component is further configured with an electro-mechanical vibrator.

In a further related embodiment, the linear actuator of the step-vibration component 310 can be configured with a step motor.

In a related embodiment, the connection pin 112 can be an integral part of the axle 330, such that the connection pin 112 is part of an outer end of the axle 330.

In various embodiments, the trigger point massage therapy device 100, can also function as and be referred to as a neuromuscular therapy device.

In various related embodiments, the pressure sensor component 311 can be an electronic pressure sensor, including well-known pressure sensors, such as piezo-resistive strain gauges, capacitive, electromagnetic, piezoelectric, or optical pressure sensors.

In various embodiments, a pressure point tip 122 124 126 128 can range in size from ⅛" to 3", and be available in a plurality of incremental sizes.

Figure 4:
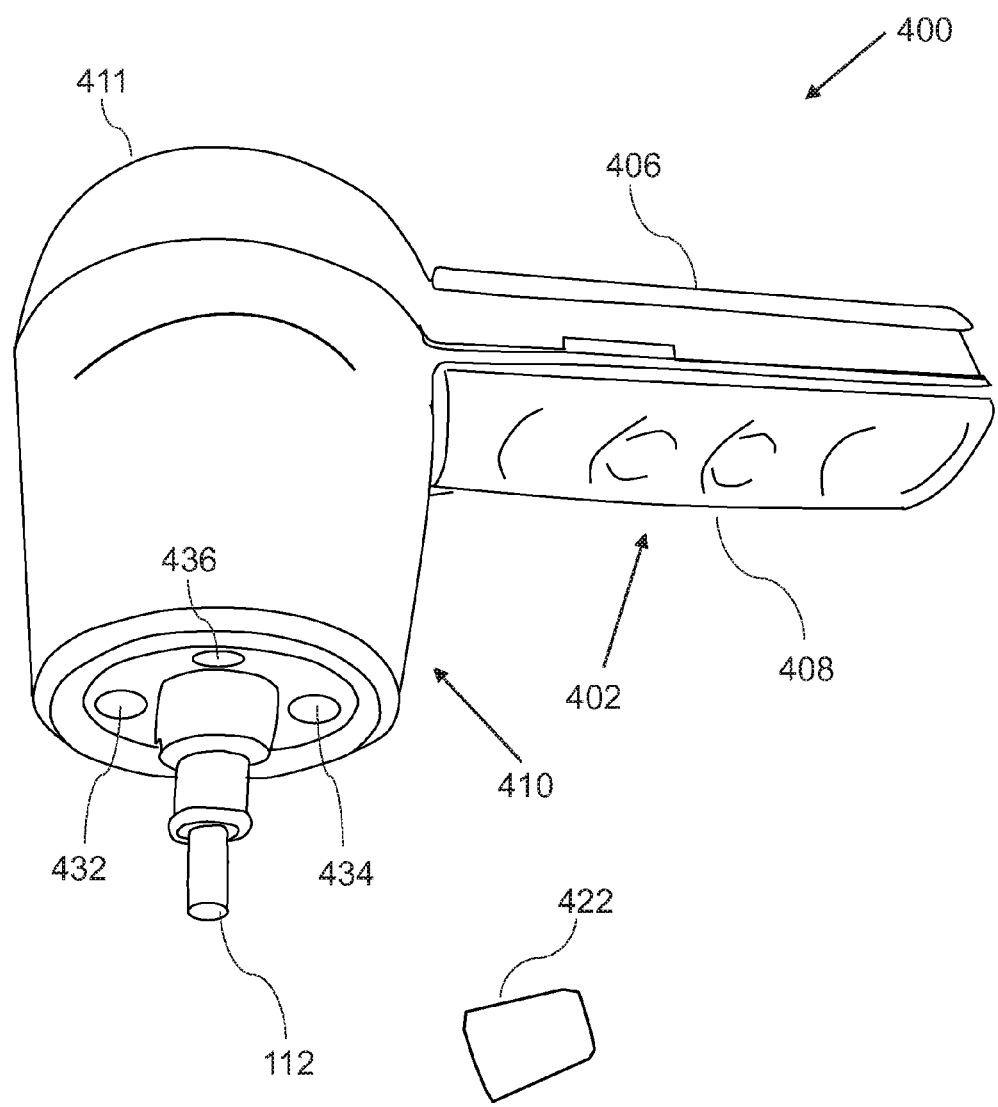
FIG. 4 is a front perspective view of a trigger point massage therapy device, according to an embodiment of the invention.

In an embodiment, FIG. 4 shows a front perspective view of an alternative design for a trigger point massage therapy device 400, comprising:
  a. A main body 410, including
    i. A soft palm pressure pad 411,
    ii. A connection pin 112;
    iii. A pressure point tip 422;
  b. A handle 402, further including:
    i. A soft rear hand grip 406;
    ii. A soft front hand grip 408.

In a related embodiment, FIG. 4 illustrates a location for an ultrasound aperture 432, for radiating ultrasound from the ultrasound component 316.

In a related embodiment, FIG. 4 illustrates a location for an infrared aperture 434, for emitting infrared radiation from the infrared component 318.

In a related embodiment, FIG. 4 illustrates a location for a cold laser light aperture 436, for emitting infrared radiation from the infrared component 318.

In a related embodiment, the pressure point tip 422 can be configured with a slide-on fastening mechanism, such that the pressure point tip 422 slides on to the connection pin 112, such that the pressure point tip 422 is held in place by a sufficiently tight grip from friction between the connection pin 112 and an inner surface of the pressure point tip 422.

In another related embodiment, the pressure point tip 422 can be configured with a screw cap fastening mechanism, to secure the pressure point tip 422 on the connection pin 112.

Figure 5:
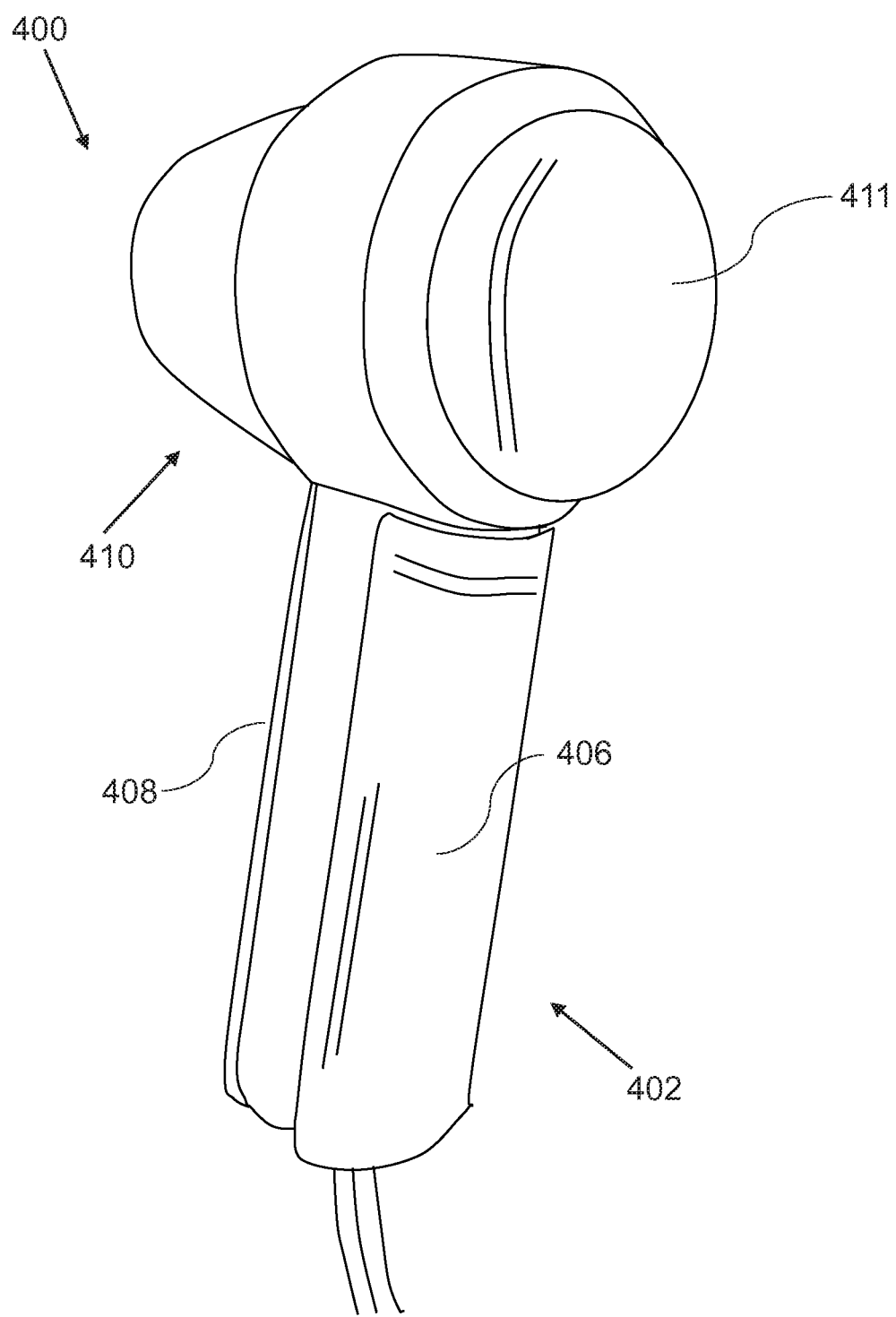
FIG. 5 is a rear perspective view of a trigger point massage therapy device, according to an embodiment of the invention.

FIG. 5 shows a rear perspective view of the trigger point massage therapy device 400.

Figure 6:
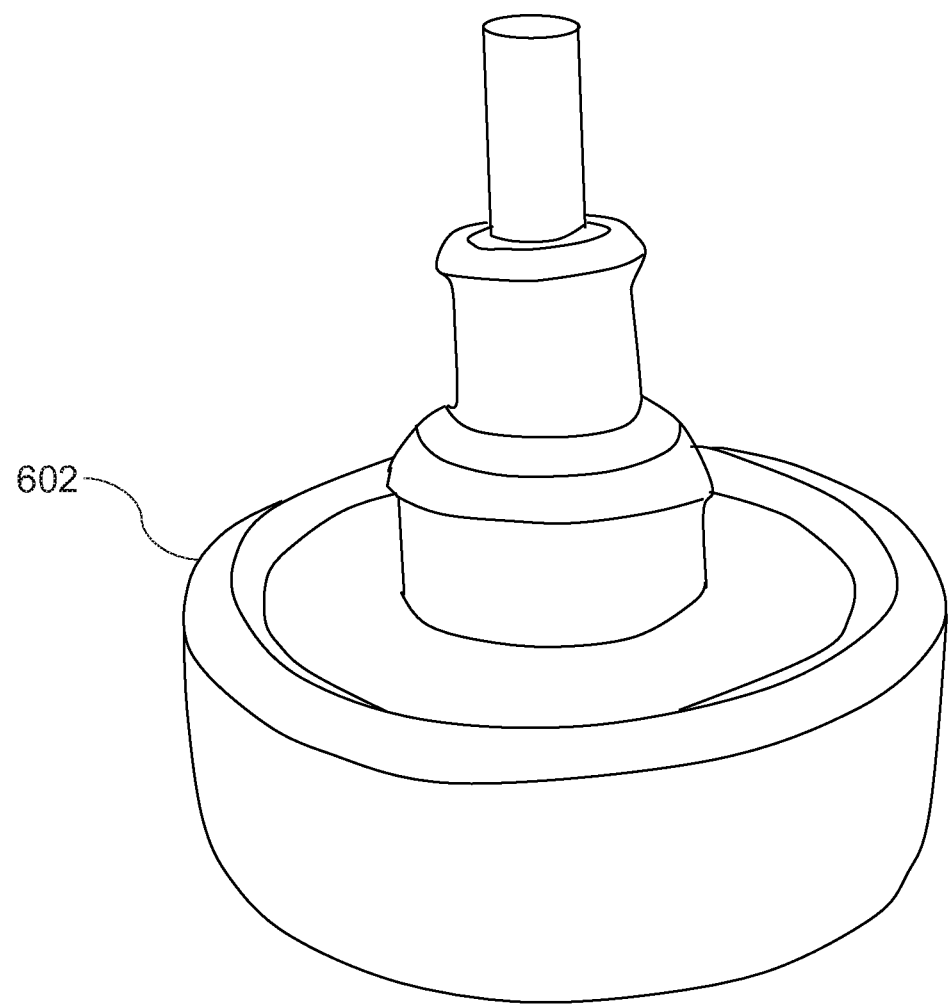
FIG. 6 is a perspective view of a front cover for a trigger point massage therapy device, according to an embodiment of the invention.

In a related embodiment, the trigger point massage therapy device 400, can further include a front cover 602, as shown in FIG. 6, which can protect a front of the main body 410 from dust and moisture, such that it covers the front, and the connection pin, such that the pressure point tip 422 (shown in FIG. 4) is mounted on the front cover 602, such that the front cover 602, is sufficiently thin and flexible to transmit pressure and vibrations. The front cover 602 can further include apertures to align with the ultrasound, infrared, and cold laser light apertures 432 434 436.

In a further related embodiment, the front cover 602 can be manufactured from a medical grade silicone rubber configured as a molded sheet with a thickness in a range from 0.25-2 mm.

Figure 7:
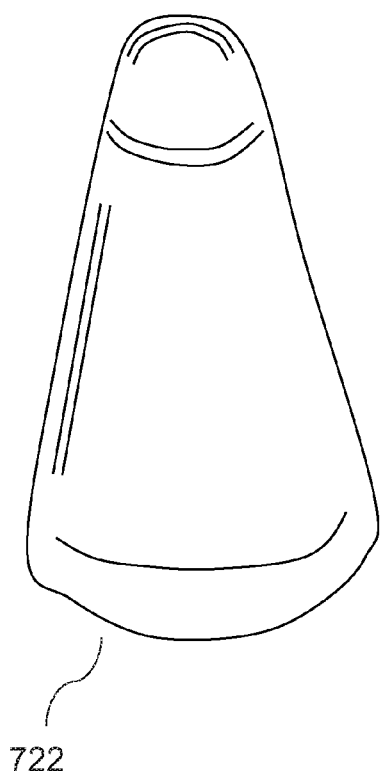
FIG. 7 is a top perspective view of a pressure point tip for a trigger point massage therapy device, according to an embodiment of the invention.
Figure 8:
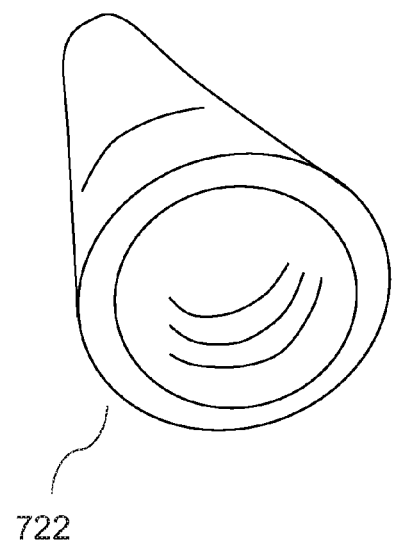
FIG. 8 is a bottom perspective view of a pressure point tip for a trigger point massage therapy device, according to an embodiment of the invention.

In a related embodiment, FIG. 7 and FIG. 8 show respectively a front and a rear perspective view of a pressure point tip 722 made from a medical grade silicone rubber.

In a related embodiment, the trigger point massage therapy device 400 can be made with a two-tone color scheme in white and grey, with silicone pressure point tips 722 made in a grey color.

Figure 9:
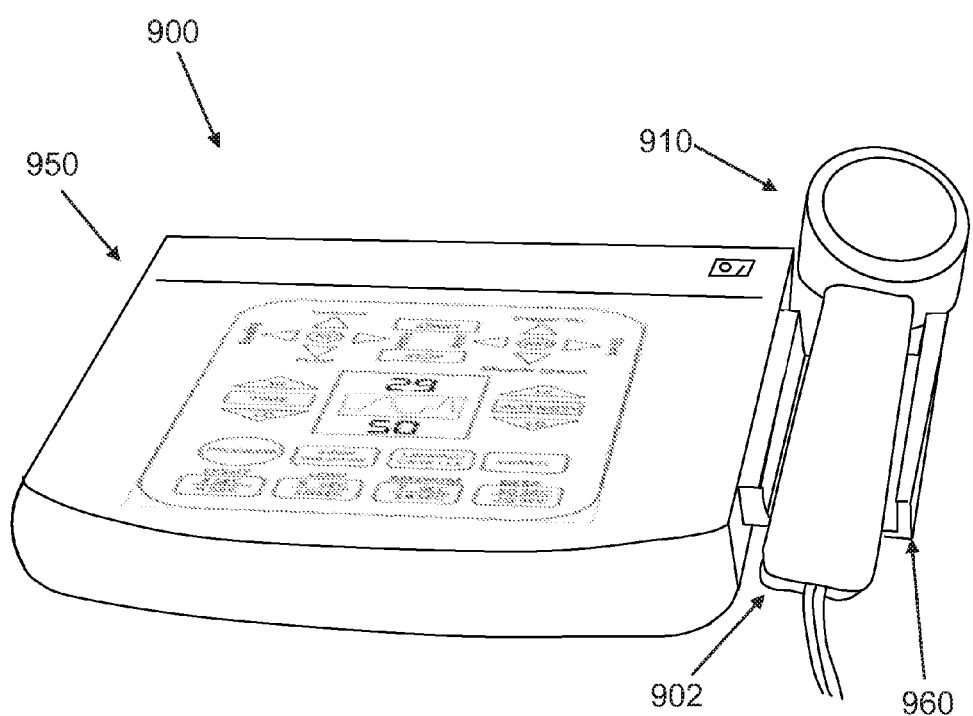
FIG. 9 is a perspective view of a trigger point massage therapy device, according to an embodiment of the invention.

In an alternative embodiment, FIG. 9 shows a desktop version of a trigger point massage therapy device 900, with a control unit 950, configured to be mounted on a table or cart surface, such that a handheld main body 910 with a handle 902 can be mounted on a side of the control unit 950, for example such that the handle 902 can rest on a hook or cradle 960, which is mounted to a side of the control unit 950.

In an embodiment, a trigger point therapy method can include:
  a. Sensing pressure applied by a therapist;
  b. Holding the pressure;
  c. Increasing the pressure; while simultaneously or sequentially:
    i. Rotating slowly a pressure point tip clock-wise or counter-clock-wise;
    ii. Vibrating the pressure point tip.

In an embodiment, a trigger point therapy method 1000, as shown in FIG. 10, can include:
  a. measuring pressure 1002, wherein a pressure is applied by a therapist using a pressure point applied to a treatment area, such that the pressure is measured with a pressure sensor during application of the pressure;
  b. adjusting the pressure 1004, wherein the pressure is adjusted by the therapist, until the pressure reaches a predetermined target value;
  c. holding the pressure 1006, wherein the pressure at the target value for a predetermined length of time; while simultaneously or sequentially:
    i. Rotating the pressure point tip 1007 clock-wise or counter-clock-wise;
    ii. Vibrating the pressure point tip 1008; and d. Increasing the pressure 1010, wherein the pressure is increased in increments.

FIG. 3 is a block diagram, including devices, systems, apparatuses, and computer program products according to various embodiments of the present invention. It shall be understood that each block or step of the block diagram, flowchart and control flow illustrations, and combinations of blocks in the block diagram, flowchart and control flow illustrations, can be implemented by computer program instructions or other means. Although computer program instructions are discussed, an apparatus or system according to the present invention can include other means, such as hardware or some combination of hardware and software, including one or more processors or controllers, for performing the disclosed functions.

In this regard, FIG. 3 depicts the computer devices of various embodiments, each containing several of the key components of a general-purpose computer by which an embodiment of the present invention may be implemented. Those of ordinary skill in the art will appreciate that a computer can include many components. However, it is not necessary that all of these generally conventional components be shown in order to disclose an illustrative embodiment for practicing the invention. The general-purpose computer can include a processing unit and a system memory, which may include random access memory (RAM) and read-only memory (ROM). The computer also may include nonvolatile storage memory, such as a hard disk drive, where additional data can be stored.

An embodiment of the present invention can also include one or more input or output components, such as a mouse, keyboard, monitor, and the like. A display can be provided for viewing text and graphical data, as well as a user interface to allow a user to request specific operations. Furthermore, an embodiment of the present invention may be connected to one or more remote computers via a network interface. The connection may be over a local area network (LAN) wide area network (WAN), and can include all of the necessary circuitry for such a connection.

Typically, computer program instructions may be loaded onto the computer or other general-purpose programmable machine to produce a specialized machine, such that the instructions that execute on the computer or other programmable machine create means for implementing the functions specified in the block diagrams, schematic diagrams or flowcharts. Such computer program instructions may also be stored in a computer-readable medium that when loaded into a computer or other programmable machine can direct the machine to function in a particular manner, such that the instructions stored in the computer-readable medium produce an article of manufacture including instruction means that implement the function specified in the block diagrams, schematic diagrams or flowcharts.

In addition, the computer program instructions may be loaded into a computer or other programmable machine to cause a series of operational steps to be performed by the computer or other programmable machine to produce a computer-implemented process, such that the instructions that execute on the computer or other programmable machine provide steps for implementing the functions specified in the block diagram, schematic diagram, flowchart block or step.

Accordingly, blocks or steps of the block diagram, flowchart or control flow illustrations support combinations of means for performing the specified functions, combinations of steps for performing the specified functions and program instruction means for performing the specified functions. It will also be understood that each block or step of the block diagrams, schematic diagrams or flowcharts, as well as combinations of blocks or steps, can be implemented by special purpose hardware-based computer systems, or combinations of special purpose hardware and computer instructions, that perform the specified functions or steps.

As an example, provided for purposes of illustration only, a data input software tool of a search engine application can be a representative means for receiving a query including one or more search terms. Similar software tools of applications, or implementations of embodiments of the present invention, can be means for performing the specified functions. For example, an embodiment of the present invention may include computer software for interfacing a processing element with a user-controlled input device, such as a mouse, keyboard, touch screen display, scanner, or the like. Similarly, an output of an embodiment of the present invention may include, for example, a combination of display software, video card hardware, and display hardware. A processing element may include, for example, a controller or microprocessor, such as a central processing unit (CPU), arithmetic logic unit (ALU), or control unit.

The many features and advantages of the invention are apparent from the detailed specification, and thus, it is intended by the appended claims to cover all such features and advantages of the invention, which fall within the true spirit and scope of the invention.

Many such alternative configurations are readily apparent, and should be considered fully included in this specification and the claims appended hereto. Accordingly, since numerous modifications and variations will readily occur to those skilled in the art, it is not desired to limit the invention to the exact construction and operation illustrated and described, and thus, all suitable modifications and equivalents may be resorted to, falling within the scope of the invention.

What is claimed is:

1. A trigger point massage therapy device, comprising:
   a) a main body, further comprising:
      a connection pin; and
      a pressure point tip, which is connected to an end of the connection pin;
      a processor;
      a non-transitory memory;
      an input/output component;
      an axle, which is connected to the connection pin; and
      a pressure sensor component, which is connected to the connection pin, and measures a pressure applied to the pressure point tip;
   b) an actual pressure indicator, which displays a current actual pressure, obtained in communication with the pressure sensor component; and
   c) a handle, which is connected to the main body;
   wherein the pressure sensor component is connected to the axle, such that the pressure sensor component measures the pressure applied to the pressure point tip, the pressure transmitted via the connection pin and the axle, such that the axle applies the transmitted pressure to the pressure sensor component;
   whereby a therapist holds the handle with a first hand, to apply pressure to a treatment area of a patient via the pressure point tip, such that the therapist adjusts the applied pressure via observation of the current actual pressure on the actual pressure indicator.

2. The trigger point massage therapy device of claim 1, wherein the main body further comprises a soft palm pressure pad, whereby the therapist applies additional pressure with a palm of a second hand pressing on the soft palm pressure pad.

3. The trigger point massage therapy device of claim 1, wherein the pressure point tip is made of a silicone material.

4. The trigger point massage therapy device of claim 1, wherein the handle further comprises a soft rear hand grip and a soft front hand grip.

5. The trigger point massage therapy device of claim 1, wherein the main body further comprises an electro-motor, which is connected to the axle, such that the electro-motor is configured to rotate the axle, both clockwise and counter-clockwise, under control by the processor.

6. The trigger point massage therapy device of claim 1, wherein the main body further comprises a step-vibration component, which is connected to the axle, such that the step-vibration component is configured to produce a vibration and a longitudinal movement of the axle, under control by the processor, such that a sequence of outward movements relative to the main body momentarily increases the pressure in increments of a predetermined duration, and such that a sequence of inward movements relative to the main body decreases the pressure.

7. The trigger point massage therapy device of claim 1, wherein the main body further comprises a heating component which is configured to heat the connection pin, under control by the processor, whereby the pressure point tip is heated.

8. The trigger point massage therapy device of claim 1, wherein the main body further comprises an ultrasound component, which is configured to target the treatment area with ultrasound.

9. The trigger point massage therapy device of claim 1, wherein the main body further comprises an infrared component, which is configured to radiate the treatment area with infrared radiation, under control of the processor.

10. The trigger point massage therapy device of claim 1, wherein the main body further comprises an electrical stimulation component, which stimulates the treatment area, via electrical stimulation transmitted via the axle and the connection pin, such that the electrical stimulation component is controlled by the processor.

11. The trigger point massage therapy device of claim 1, wherein the main body further comprises a cold laser light component, which is configured to radiate the treatment area with cold laser light, under control of the processor.

12. The trigger point massage therapy device of claim 1, further comprising a control unit, which is connected to the main body, such that the control unit is configured to control the trigger point massage therapy device.

13. The trigger point massage therapy device of claim 1, further comprising a target pressure indicator, which displays a targeted pressure, wherein the targeted pressure is obtained from pre-determined settings.

14. The trigger point massage therapy device of claim 1, further comprising a pressure status graph indicator, such that the pressure status graph indicator displays a historical graph of pressure applied during a predetermined past time period, and such that the pressure status graph indicator displays a planned graph of pressure planned during a predetermined future time period.

15. The trigger point massage therapy device of claim 1, further comprising a front cover, which protects a front of the main body from dust and moisture, such that the front cover covers the front and the connection pin, such that the pressure point tip is mounted on the front cover, such that the front cover is configured to transmit pressure and vibrations from the pressure point tip to the connection pin.

16. The trigger point massage therapy device of claim 15, wherein the front cover is manufactured with a medical grade silicone rubber configured as a molded sheet with a thickness in a range from 0.25 2 mm.

17. The trigger point massage therapy device of claim 1, wherein the connection pin further comprises a fastening mechanism, such that the pressure point tip is connected to the end of the connection pin with the fastening mechanism.

18. A trigger point massage therapy device, comprising:
a) a main body, further comprising:
 a connection pin; and
 a pressure point tip, which is connected to an end of the connection pin;
b) a pressure sensor component, which is connected to the connection pin, and measures a pressure applied to the pressure point tip;
c) an actual pressure indicator, which displays a current actual pressure, obtained in communication with the pressure sensor component;
d) a handle, which is connected to the main body; and
e) a pressure status graph indicator;
such that the pressure status graph indicator displays a historical graph of pressure applied during a predetermined past time period, and such that the pressure status graph indicator displays a planned graph of pressure planned during a predetermined future time period;
whereby a therapist holds the handle with a first hand, to apply pressure to a treatment area of a patient via the pressure point tip, such that the therapist adjusts the applied pressure via observation of the current actual pressure on the actual pressure indicator.

19. A trigger point therapy method of using a trigger point massage therapy device, comprising the acts of:
a) measuring a pressure, wherein the pressure is applied by a therapist using a pressure point tip applied to a treatment area, such that the pressure is measured with a pressure sensor during application of the pressure;
b) adjusting the pressure, wherein the pressure is adjusted by the therapist, until the pressure reaches a predetermined target pressure value; and
c) holding the pressure, wherein the pressure is at the predetermined target pressure value for a predetermined length of time;
wherein the trigger point massage therapy device comprises:
a main body, further comprising:
 a connection pin; and
 the pressure point tip, which is connected to an end of the connection pin;
a processor;
a non-transitory memory;
an input/output component;
an axle, which is connected to the connection pin; and
a pressure sensor component, which is connected to the connection pin, and measures a pressure applied to the pressure point tip;
an actual pressure indicator, which displays a current actual pressure, obtained in communication with the pressure sensor component; and
a handle, which is connected to the main body;
wherein the pressure sensor component is connected to the axle, such that the pressure sensor component measures the pressure applied to the pressure point tip, the pressure transmitted via the connection pin and the axle, such that the axle applies the transmitted pressure to the pressure sensor component.

20. The trigger point therapy method of claim 19, wherein the act of holding the pressure further comprises rotating the pressure point tip.

21. The trigger point therapy method of claim 19, wherein the act of holding the pressure further comprises vibrating the pressure point tip.

22. The trigger point therapy method of claim 19, further comprising:
    increasing the pressure, wherein the pressure is increased in increments.

* * * * *